United States Patent [19]

Petros

[11] Patent Number: 5,112,344

[45] Date of Patent: May 12, 1992

[54] SURGICAL INSTRUMENT AND METHOD OF UTILIZATION OF SUCH

[76] Inventor: Peter E. Petros, 3 Wilson Street, Claremont, Australia, 6010

[21] Appl. No.: 654,648

[22] PCT Filed: Oct. 4, 1989

[86] PCT No.: PCT/AU89/00432

§ 371 Date: Feb. 11, 1991

§ 102(e) Date: Feb. 11, 1991

[87] PCT Pub. No.: WO90/03766

PCT Pub. Date: Apr. 19, 1990

[30] Foreign Application Priority Data

Oct. 4, 1988 [AU] Australia ............................. PJ0756

[51] Int. Cl.⁵ ..................... A61B 17/04; A61B 19/00; A61F 2/02
[52] U.S. Cl. ................... 606/148; 606/144; 600/30; 128/DIG. 25
[58] Field of Search ................... 600/29–31; 606/139, 144–150, 170, 171; 128/885, DIG. 25

[56] References Cited

U.S. PATENT DOCUMENTS

| | | | |
|---|---|---|---|
| 2,897,820 | 8/1959 | Tauber | 606/148 |
| 3,372,695 | 3/1968 | Beliveau et al. | 600/29 |
| 3,763,860 | 10/1973 | Clarke | 128/830 |
| 4,235,238 | 11/1980 | Ogiu et al. | 606/145 |
| 4,392,495 | 7/1983 | Bayers | 606/148 |
| 4,493,323 | 1/1985 | Albright et al. | 606/144 |
| 4,857,041 | 8/1989 | Annis et al. | 600/30 |

Primary Examiner—Ronald Frinks
Attorney, Agent, or Firm—Stevens, Davis, Miller & Mosher

[57] ABSTRACT

A method of treating female incontinence comprising looping a filamentary element (19) between the wall of the vagina (16) and the rectus abdominis sheath in the anterior wall of the abdomen whereby it passes to each side of the urethra (20) into the correct spatial relationship to the pubis (17), allowing the development of scar tissue between the vaginal wall (16) and the rectus abdominis sheath and removing the filamentary element (19). A surgical instrument for use with the method comprises a surgical instrument for the application of a filamentary element (19) into the body for the purpose of treating female incontinence, said instrument comprising a tubular shaft (11) having a handle (12) at one end and carried toward its other end a flexible needle element (13) slidably receivable in the shaft (11) and adapted at one end to receive a filamentary element (19) and having an enlarged profiled portion (15) at its other end whereby when the needle element (13) is received in the shaft (11) the other end of the needle element (13) defines a convergent surface of the other end of the shaft (11) and the one end of the needle element (13) is exposed at the one end of the shaft (11).

3 Claims, 4 Drawing Sheets

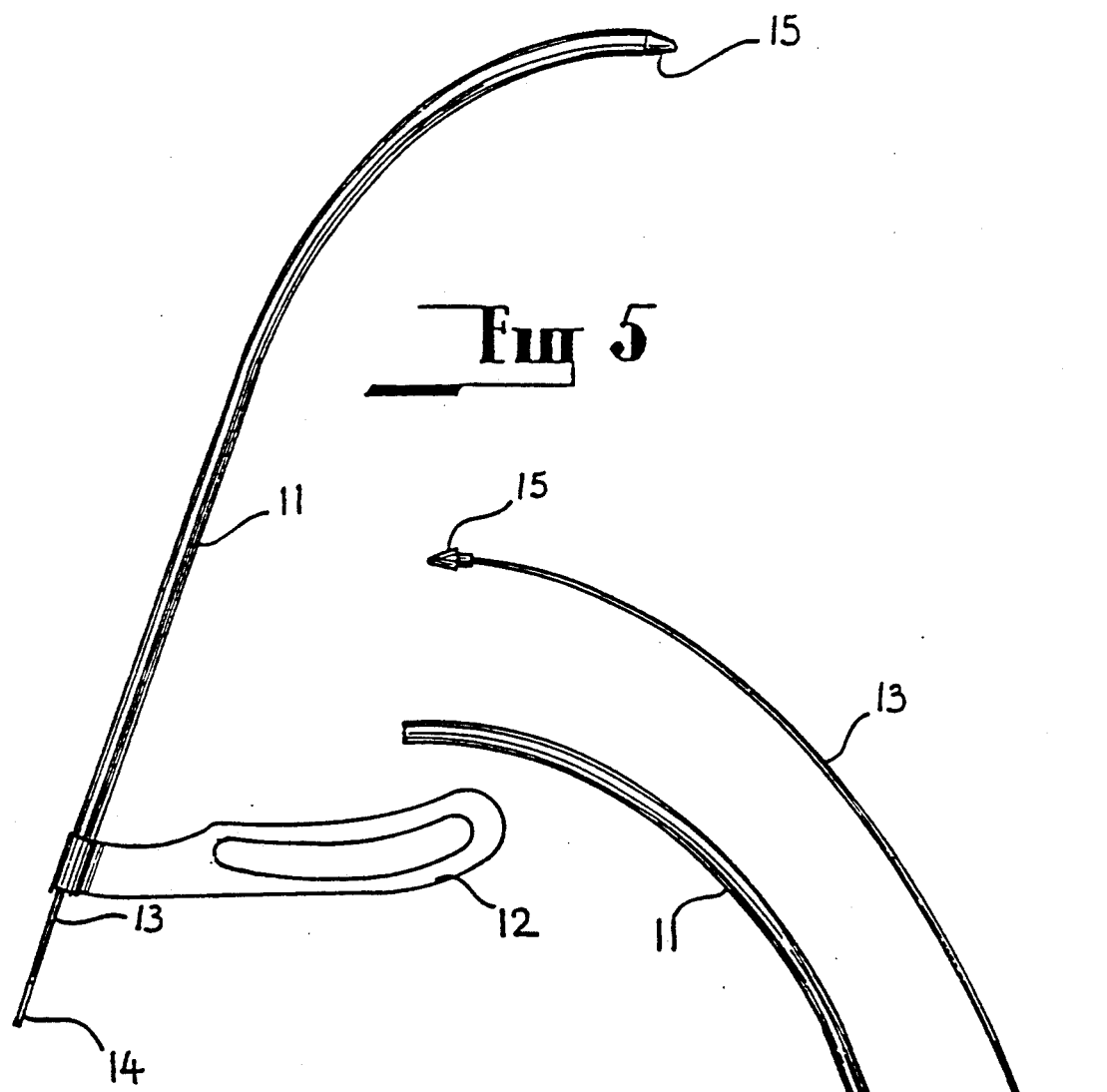

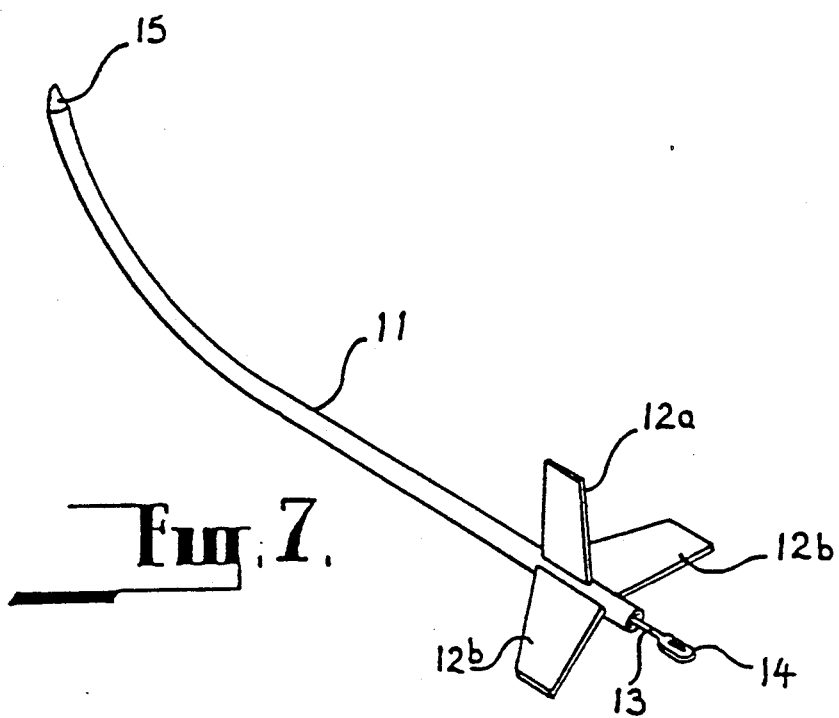
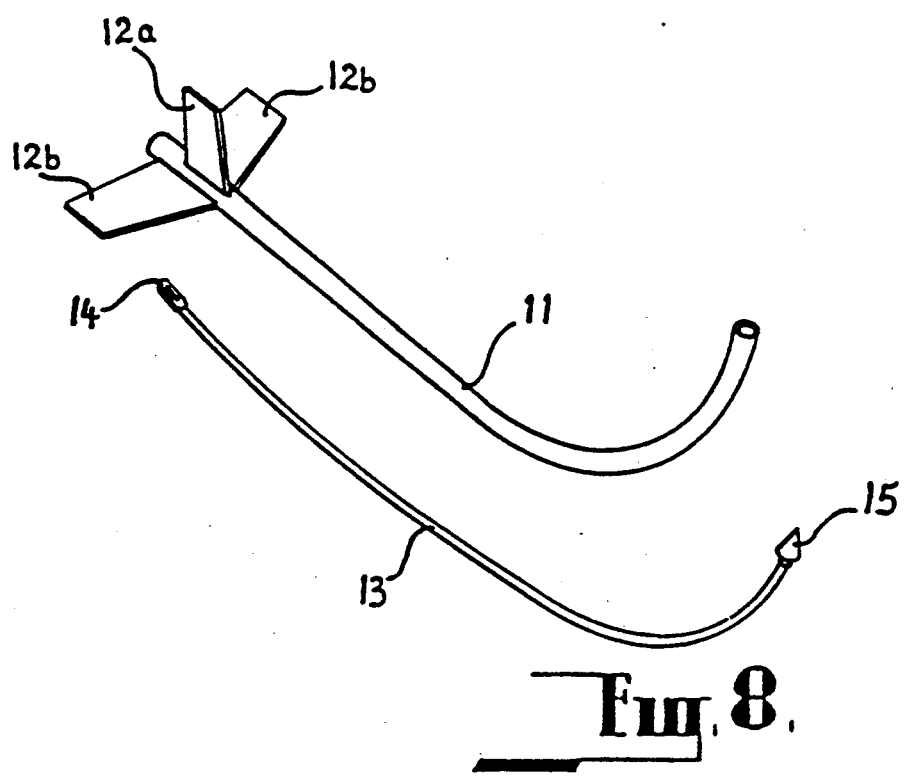

SURGICAL INSTRUMENT AND METHOD OF UTILIZATION OF SUCH

This invention relates to a surgical instrument for use in the treating of female incontinence and to a method of treating such incontinence.

In one form the invention resides in a surgical instrument for the application of a filamentary element into the body for the purpose of treating female incontinence, said instrument comprising a substantially rigid linear tubular shaft having a handle at one end and being curved towards its other end to form a curved portion, a flexible needle element slidably received in the shaft and adapted at one end to receive a filamentary element and having an enlarged portion at its other end, whereby when the needle element is fully received in the shaft the enlarged portion of the needle defines a non-incisive convergent surface at the other end of the shaft and the one end of the needle element is exposed at the one end of the shaft, the shaft being dimensioned and curved towards its other end whereby when in use and in position the curved portion extends from the anterior vaginal wall to the anterior surface of the abdomen past the pubis.

In another form the invention resides in a method of treating female incontinence comprising looping a filamentary element between the wall of the vagina and the rectus abdominis sheath in the anterior wall of the abdomen whereby it passes to each side of the urethra, tightening the loop to bring the vaginal wall and the urethra into the correct spatial relationship to the pubis allowing the development of scar tissue between the vaginal wall and the anterior wall of the abdomen pubic symphysis and removing the filamentary element.

The invention will be more fully understood in the light of the particular embodiment of the invention described below. The description is made with reference to the accompanying drawings of which:

FIG. 5 is a side elevation of the embodiment;

FIG. 6 is a side elevation of the embodiment with the needle element removed;

FIG. 7 is an isometric view of an alternative form of the embodiment; and

FIG. 8 is an isometric view of the form of the embodiment of FIG. 7 with the needle removed.

Figure 1:
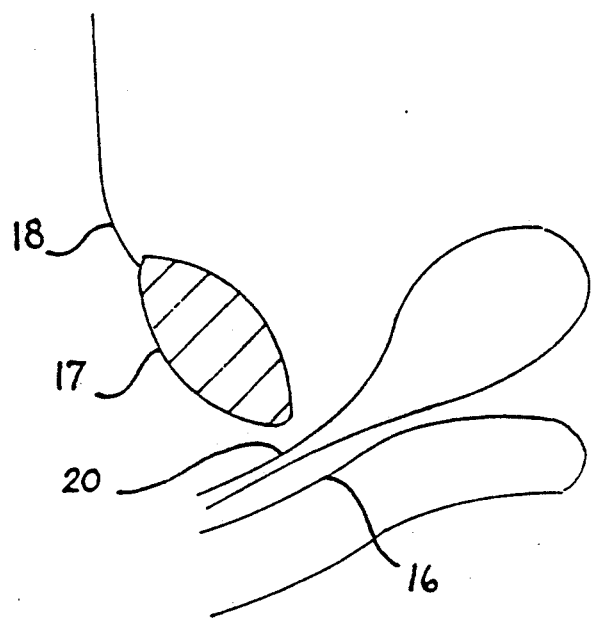
FIG. 1 is a schematic sagital section illustrating the circumstance which the urethro vesical junction wall is in a state of prolapse.

The embodiment is directed to a surgical tool for the treatment of female incontinence whereby as a result of the deterioration of the tissue or ligaments interconnecting the pubis with the vaginal wall. Such a condition can level to a loss of control of emissions from the urethra. The embodiment relates to an apparatus whereby the vaginal wall and urethra can be brought into a proper spatial relation with the pubis in order to restore continence. The embodiment comprises a surgical tool two forms of which are shown at FIGS. 5 and 6 and 7 and 8 which comprise a tubular shaft 11 having a handle 12 at one end and curved at its other end to a configuration approximately corresponding to the general curvature of the pubis between the vaginal wall and the anterior surface of the abdomen. As shown at FIGS. 7 and 8 which are directed to an alternative form of the invention the handle 12 may comprise a central radial arm 12a which is in the plane of curvature of the shaft to provide a positioning guide. The handle further comprises a pair of opposed arms 12b equally angularly offset from the central radial arm 12a. The opposed arms 12b provide facility for applying some leverage which may be required in using the instrument. The tubular shaft accommodates a needle element 13 which is provided at one end with an eye 14 for receipt of a filamentary element (not shown). The other end of the needle element is formed with an enlarged conically shaped head portion 15 which is receivable at the other end of the shaft 11 to close the other end of the shaft and define a convergent substantially conical surface to facilitate penetration of the instrument through the body cavity.

Figure 2:
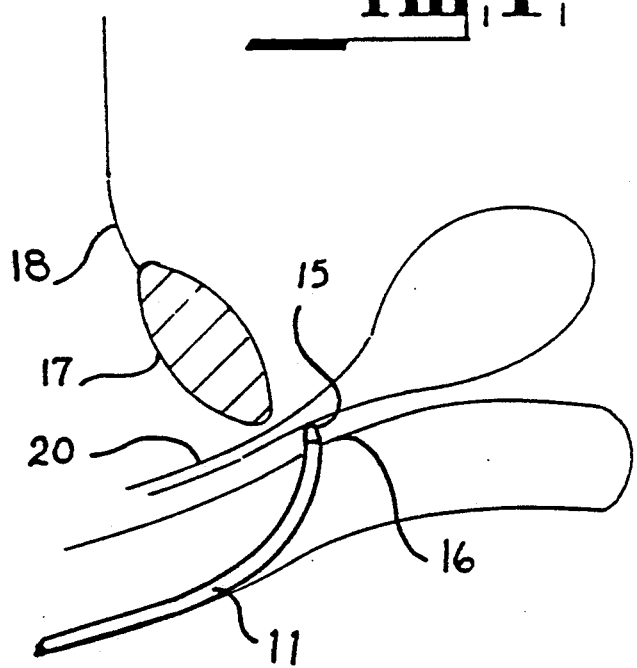
FIGS. 2, 3 and 4 are sagital sections illustrating the stages entry of the embodiment into the body.
Figure 3:
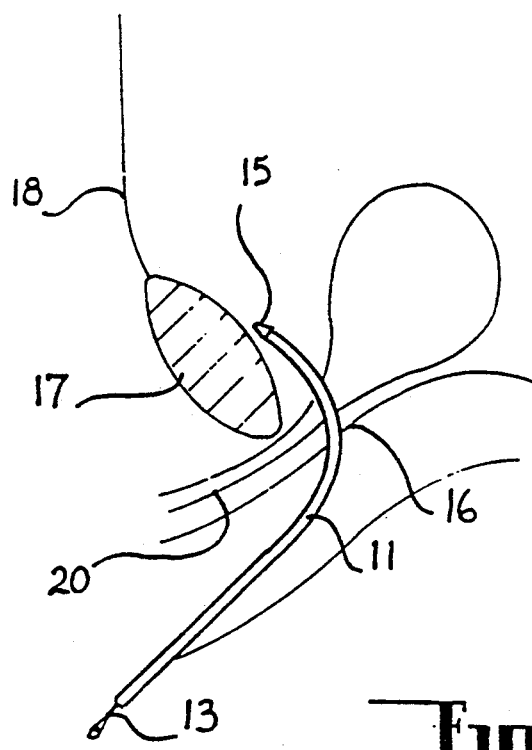
Figure 4:
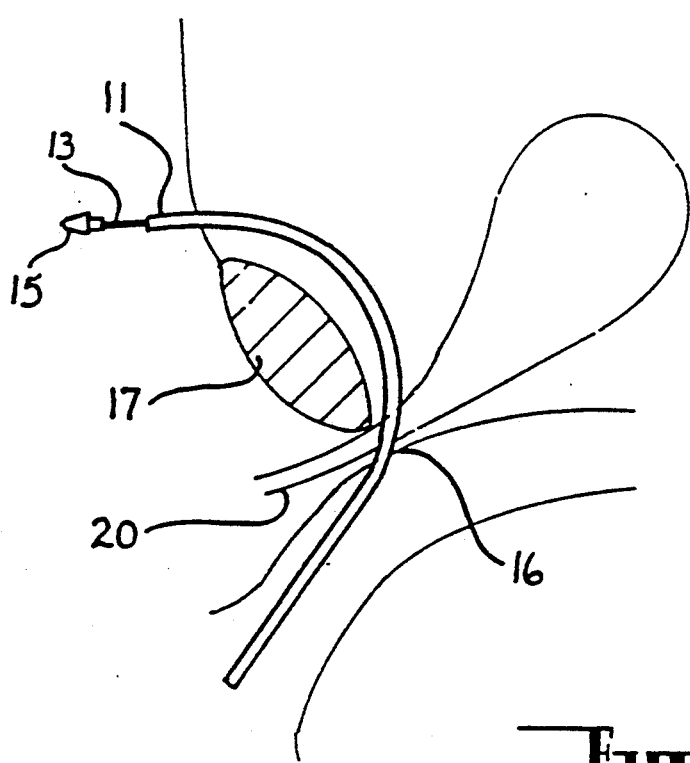

In using the instrument and as shown at FIGS. 2, 3 and 4 an incision is made in the vaginal wall 16 in the region of the urethro vesical junction. The other end of the instrument, having the needle element 13 therein, is passed through the incision made in the vaginal wall 16 and is passed through the body cavity around the pubis 17 until it contacts the muscle tissue 18 at the anterior wall of the abdomen. An incision is then made into the body wall at the point of contact of the other end of the instrument to allow passage of the instrument through the muscle tissue. A filamentary element 19 which takes the form of a tape is then applied through the eye of the needle element 13 and the needle element is withdrawn from the shaft such that the filamentary element 19 is pulled through the shaft. With the filamentary element 19 in place the shaft is then removed from the body while the filamentary element is stationary. A second incision is made into the vaginal wall 16 to the other side of the urethra 20. The surgical instrument having the needle element in place in the shaft is then inserted into the second incision and again the shaft 11 is passed through the body cavity until it contacts the muscle tissue 18 at the interior wall of the abdomen at a position spaced from the first incision in the muscle wall at which time a second incision is made in the anterior wall of the abdomen through which the other end of the surgical instrument is passed. The needle element is then removed from the shaft while the shaft is held in position and the end of the filamentary element which is in place in the body is then engaged through the eye of the needle element. The needle is then reinserted into the shaft such that the filamentary element 19 is carried to the one end of the shaft where it is disconnected from the needle element 13. The needle element is then removed from the shaft 11. The shaft is then removed from the body while the filamentary element remains stationary. As a result the filamentary element is then looped around the muscle tissue 18 of the abdomen to either side of the urethra 20 with the ends extending into the vagina.

The filamentary element is left in place for a sufficient period of time for a scar tissue to develop around the filamentary element which provides a ligament like interconnection between the vaginal wall and the muscle tissue at the anterior surface of the abdomen. After satisfactory development of such tissue the ends of the filamentary element are disconnected and the filamentary element is removed from the body per vagina.

The claims defining the invention are as follows:

1. A surgical instrument for the application of a filamentary element into the body for the purpose of treating female incontinence, said instrument comprising a substantially rigid linear tubular shaft having a handle at one end and being curved towards its other end to form a curved portion, a flexible needle element slidably received in the shaft and adapted at one end to receive a filamentary element and having an enlarged portion at its other end, whereby when the needle element is fully received in the shaft the enlarged portion of the needle defines a non-incisive convergent surface at the other end of the shaft and the one end of the needle element is exposed at the one end of the shaft, the shaft being dimensioned and curved towards its other end whereby when in use and in position the curved portion extends from the anterior vaginal wall to the anterior surface of the abdomen past the pubis.

2. A surgical instrument as claimed at claim 1 wherein the curvature of the shaft approximates the general profile of the pubis between the vagina and the anterior surface of the abdomen.

3. A method of treating female incontinence comprising looping a filamentary element between the wall of the vagina and the rectus abdominis sheath in the anterior wall of the abdomen whereby it passes to each side of the urethra into the correct spatial relationship to the pubis, allowing the development of scar tissue between the vaginal wall and the rectus abdominis sheath and removing the filamentary element.

* * * * *